(12) United States Patent
Kopkalli et al.

(10) Patent No.: US 10,851,032 B2
(45) Date of Patent: Dec. 1, 2020

(54) DEHYDROHALOGENATION REACTOR AND PROCESS

(71) Applicant: HONEYWELL INTERNATIONAL INC., Morristown, NJ (US)

(72) Inventors: Haluk Kopkalli, Staten Island, NY (US); Ron Joseph Roof, Center Valley, PA (US); Yuon Chiu, Denville, NJ (US); Hsueh Sung Tung, Getzville, NY (US); Robert A. Smith, Kinnelon, NJ (US); Haiyou Wang, Amherst, NY (US)

(73) Assignee: Honeywell International Inc., Charlotte, NC (US)

(*) Notice: Subject to any disclaimer, the term of this patent is extended or adjusted under 35 U.S.C. 154(b) by 0 days.

(21) Appl. No.: 15/768,270

(22) PCT Filed: Oct. 14, 2016

(86) PCT No.: PCT/US2016/057089
§ 371 (c)(1),
(2) Date: Apr. 13, 2018

(87) PCT Pub. No.: WO2017/066603
PCT Pub. Date: Apr. 20, 2017

(65) Prior Publication Data
US 2018/0297917 A1   Oct. 18, 2018

Related U.S. Application Data

(60) Provisional application No. 62/241,992, filed on Oct. 15, 2015.

(51) Int. Cl.
*C07C 17/25* (2006.01)
*C07C 21/18* (2006.01)
(Continued)

(52) U.S. Cl.
CPC ............. *C07C 17/23* (2013.01); *B01J 8/0221* (2013.01); *B01J 8/065* (2013.01); *B01J 8/067* (2013.01);
(Continued)

(58) Field of Classification Search
None
See application file for complete search history.

(56) References Cited

U.S. PATENT DOCUMENTS 3,484,502 A   12/1969   McCarthy
4,413,041 A   11/1983   Hegedus
(Continued)

OTHER PUBLICATIONS

Electric Furnace: Merriam-Webster definition.*
(Continued)

*Primary Examiner* — Medhanit W Bahta
(74) *Attorney, Agent, or Firm* — Faegre Drinker Biddle & Reath LLP

(57) ABSTRACT

The invention provides a reactor comprising a reaction chamber having a catalytic surface in contact with reactants in said chamber, and a source for passing electrical current through said catalytic surface. The reactor can be used for dehydrohalogentation reactions, such as dehydrochlorination of HCFC-244bb to HFO-1234yf and for reactions where zero valent metals are employed for catalysis. The invention further provides a process to prepare HFO-1234yf from HCFC-244bb using an electrically heated reaction chamber.

18 Claims, 4 Drawing Sheets

(51) Int. Cl.
*C07C 17/23* (2006.01)
*B01J 23/745* (2006.01)
*B01J 23/755* (2006.01)
*B01J 15/00* (2006.01)
*B01J 19/24* (2006.01)
*B01J 16/00* (2006.01)
*B01J 8/06* (2006.01)
*B01J 8/02* (2006.01)
*B01J 23/72* (2006.01)
*C07C 17/42* (2006.01)

(52) U.S. Cl.
CPC ........... *B01J 15/005* (2013.01); *B01J 16/005* (2013.01); *B01J 19/24* (2013.01); *B01J 19/242* (2013.01); *B01J 23/72* (2013.01); *B01J 23/745* (2013.01); *B01J 23/755* (2013.01); *C07C 17/25* (2013.01); *C07C 17/42* (2013.01); *B01J 2208/00407* (2013.01); *B01J 2208/00415* (2013.01); *B01J 2208/06* (2013.01); *B01J 2219/00132* (2013.01); *B01J 2219/00135* (2013.01); *B01J 2219/00763* (2013.01); *Y02P 20/582* (2015.11)

(56) References Cited

U.S. PATENT DOCUMENTS

| | | |
|---|---|---|
| 8,058,486 B2 | 11/2011 | Merkel et al. |
| 2009/0043136 A1 | 4/2009 | Wang et al. |
| 2015/0005536 A1* | 1/2015 | Wang ..................... B01J 27/08 570/179 |
| 2015/0183698 A1 | 7/2015 | Merkel et al. |
| 2015/0247674 A1* | 9/2015 | Nappa .................... C07C 17/25 51/296 |
| 2015/0259266 A1 | 9/2015 | Takahashi et al. |
| 2019/0084905 A1* | 3/2019 | Wang ................... C07C 17/087 |

OTHER PUBLICATIONS

International Search Report dated Jan. 11, 2017 issued in PCT/US2016/057089.

Pu, Zhi-Ying et al., "Vapor phase fluorination of 1, 1, 1-trifluoro-2-chloroethane over CrOx-Y2O3 catalysts: Effects of calcination atmosphere and chromium content," Indian Journal of Chemistry (Dec. 2011) vol. 50A, No. 12, pp. 1719-1724.

* cited by examiner

DEHYDROHALOGENATION REACTOR AND PROCESS

CROSS REFERENCE TO RELATED APPLICATION

This application is a '371 of International Application No. PCT/US2016/057089, which was filed on Oct. 14, 2016, which claims benefit of U.S. Provisional Application having Ser. No. 62/241,992, filed on Oct. 15, 2015, the contents of both of which are incorporated by reference.

FIELD OF THE DISCLOSURE

The invention relates to an electrically heated reactor. Without limitation, the reactor can be used in dehydrohalogenation reactions, and can be of diverse configurations, including tubular design.

BACKGROUND OF THE DISCLOSURE

Fluorocarbons, particularly fluorinated olefins, as a class, have many and varied uses, including as chemical intermediates and monomers. In particular, these products are useful as refrigerants, monomers or intermediates for preparing refrigerants, particularly those identified as having low global warming potential.

With concerns over global warming, hydrofluoroolefins (HFOs) are being commercialized as substitutes for chlorofluorocarbons (CFCs), hydrochlorofluorocarbons (HCFCs) and hydrofluorocarbons (HFCs) for use as refrigerants, heat transfer agents, blowing agents, monomers and propellants because HFOs do not deplete the ozone layer and have low global warming potential. Some HFOs are prepared by multiple steps that involve fluorinating a chlorinated organic compound with a fluorination agent such as hydrogen fluoride in the presence of a fluorination catalyst. These reactions may be conducted in either the liquid or gas phase or a combination of these.

In one process to manufacture HFO-1234yf (2,3,3,3-tetrafluoro-1-propene), the following reaction sequence is known:

Step (1): $1230xa+3HF \rightarrow 1233xf+3HCl$
(where 1230xa is $CCl_2=CClCH_2Cl$ and 1233xf is $CH_2=CClCF_3$)

Step (2): $1233xf+HF \rightarrow 244bb$
(where 244bb is $CH_3CClFCF_3$)

Step (3): $244bb \rightarrow 1234yf+HCl$
(where 1234yf is $CH_2=CFCF_3$)

In a preferred practice, Step (1) takes place in the gas phase in the presence of a fluorination catalyst; Step (2) takes place in the liquid phase in the presence of a fluorination catalyst; and Step (3) takes place in the gas phase in the presence or absence of a dehydrochlorination catalyst.

The Step (3) reaction is endothermic, with a heat of reaction of approximately 15 kcal/mol or 180 BTU/lb of HCFC-244bb. The reaction typically takes place at about 450° C. to about 480° C. The reaction is catalyzed by the metal in the reactor (reactor walls, catalyst in the form of metal pellets, mesh, etc). This method is representatively disclosed in US Patent Application Publication No. 2009/0043136, the entire contents of which are incorporated herein by reference.

In addition to being endothermic, Step (3) requires a high temperature to initiate. But overheating the process material or heat transfer surfaces can lead to high rates of coke or carbon formation, necessitating frequent shutdowns in order to clean the reactor system. A conventional approach to designing a reaction system useful for Step (3) typically includes the following:

1) A superheater to heat the reactants;
2) An isothermal shell and tube reactor, with heat exchange medium on the shell;
3) A limited conversion per pass in the reactor;
4) Utility to superheat, and utility to enable heat input to the reactor shell; and
5) Means to regenerate catalytic surfaces (if applicable)

These approaches require a system with many components of inherent complexity. One example is the use of a molten salt system to heat the reactor. Such a system includes, at a minimum: a reactor, a superheater, a fired heater, a molten salt tank, and molten salt pumps. Because the salt required for such a system freezes at a high temperature (in the range of 240° C.), additional complex means must be incorporated to start up the system while keeping the salt molten during initial contact with the cold surfaces of the reactor, such means may include a system to dilute the salt during startup, or extensive use of jacketing and/or heat tracing.

Another problem with a molten salt system is the requirement that heating be evenly applied throughout the reactor, since lower local temperatures will result in loss of reaction efficiency, while higher local temperatures will lead to coking of the heat transfer surfaces, also leading to loss of efficiency. Overcoming these difficulties requires a very large flow of molten salt, which, in turn, leads to high capital and operating costs associated with the large pumps and piping needed.

Thus, a simplified system with less equipment is desirable.

SUMMARY

In one aspect, the invention is to a reactor comprising a reaction chamber having a catalytic surface in contact with reactants in said chamber, and a source for passing electrical current through said catalytic surface. In one practice, this electrical current provides the necessary heat for the reaction to occur. In one practice, the electrical current heats the reactants, and the metal surface through which the current passes catalyzes the reaction; an example of such a reaction is, without limitation, a dehydrohalogenation reaction, including the dehydrochlorination of HCFC-244bb to HFO-1234yf, although other reactions are contemplated, e.g. those catalyzed by zero valent metals, and including pyrolysis reactions. The electrical current may be alternating current or direct current. The reactor can be comprised of tubes or pipes, such as found in a shell and tube configuration. In an embodiment, one or more of the tubes or pipes may be finned, while in another embodiment, none of the tubes of the tubes or pipes are finned. Thus, in an embodiment, all of the tubes or pipes are smooth, while in another embodiment, at least one of the tubes or pipes is smooth. The electrical current can be passed through the surface of the pipes and/or through packing disposed inside or outside the pipes or otherwise in the reactor in order to provide reactor heating. The reactor may further comprise, or, optionally, be in fluid communication with, a superheater to bring the reactants up to or the reaction temperature prior to entering the reactor where the catalysis occurs.

In another aspect, the invention is to a process for preparing unsaturated hydrofluorocarbons such as HFO-1234yf, HFO-1234ze, HCFO-1233zd, HFO-1243zf, trifluoropropyne, and the like. In one such practice, the invention is to a process for preparing 2,3,3,3-tetrafluoropropene (HFO-1234yf) comprising providing a composition comprising 2-chloro-1,1,1,2-tetrafluoropropane (HCFC-244bb) to a reaction chamber having a catalytic surface in contact with the composition, the reaction chamber being connected to an electrical power source; and passing electrical current from the power source through the catalytic surface effective to heat the catalytic surface to a temperature effective to catalytically dehydrochorinate at least a portion of the HCFC-244bb to HFO-1234yf.

The invention provides a simplified reaction system for a highly reliable apparatus useful for heating reactors where high temperatures and even process heating are required.

The advantages of the present invention include, without limitation, process simplification, which results in a more economical and reliable process; uniform heat input across the heat transfer surfaces, which maximizes reaction efficiency while at the same time minimizes coking; simple and rapid startup; and improved process safety. Advantageously, it has been surprisingly found that when direct current is used to heat the reactor, the catalytic rate is improved.

DETAILED DESCRIPTION

As described in U.S. Pat. No. 8,058,486, the contents of which are incorporated herein by reference, HCFC-244bb feed can be formed from HCFO-1233xf hydrofluorination in a liquid phase reactor in the presence of a fluorination catalyst. Due to incomplete conversion of HCFO-1233xf and its close boiling point to HCFC-244bb as well as the formation of azeotrope or azeotrope-like composition of HCFC-244bb and HCFO-1233xf under certain conditions, the separation of these two compounds is difficult. For this reason, the HCFC-244bb feed generally contains certain amount of HCFO-1233xf.

Figure 1:
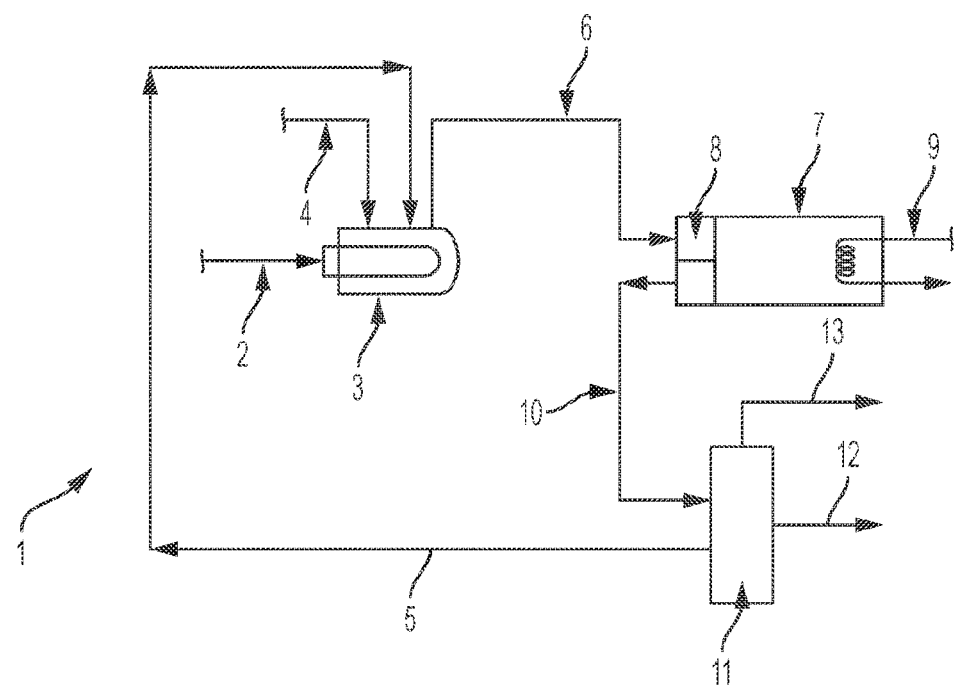
FIG. 1 is a schematic of a process flow embodying the reactor of the present invention. The scheme illustrates a practice employing a vaporizer and a separation step and is shown in the context of preparing HFO-1234yf by dehydrochlorination of HCFC-244bb.

In one practice, the reactor is used in preparing HFO-1234yf by dehydrochlorination of HCFC-244bb. FIG. 1 depicts an exemplary process flow scheme 1 for such a reaction. The process depicted utilizes only an electric heater 9 in reactor 7, which in this embodiment is designed to have a superheater zone 8, thus the reactor both superheats the reactants comprising HCFC-244bb and reacts same catalytically to form product comprising HFO-1234yf. While FIG. 1 depicts a single stage reactor, multistage electrically heated reactors are also contemplated. The power source 9 electrically provides the heat for reaction, and furnishes alternating or direct current (rectifiers and/or transformers as may be needed not shown). In FIG. 1, fresh feed 4 comprising liquid HFC-244bb, and recycle HCFC-244bb from separation step 12, are fed to vaporizer 3 which is heated using steam 2 or other suitable media, e.g. electrically heated. Vaporized HCFC-244bb exits the vaporizer at 6 and is fed to reactor 7. Reactor 7, an exemplary schematic depiction of which is in FIG. 2, can have any suitable configuration, including various shell and tube (e.g. fixed tube, U-tube, etc.) or other configurations as known in the art. Electrically-heated reactor 7 can be comprised of a single stage or multiple stages. Prior to being introduced into the reactor, the process gases including reactants and recycle, can be preheated to the reaction temperature, e.g. from about 450° to about 480° C. in the case of converting HCFC-244bb to HFO-1234yf, by an additional electric heater of appropriate design.

Figure 2:
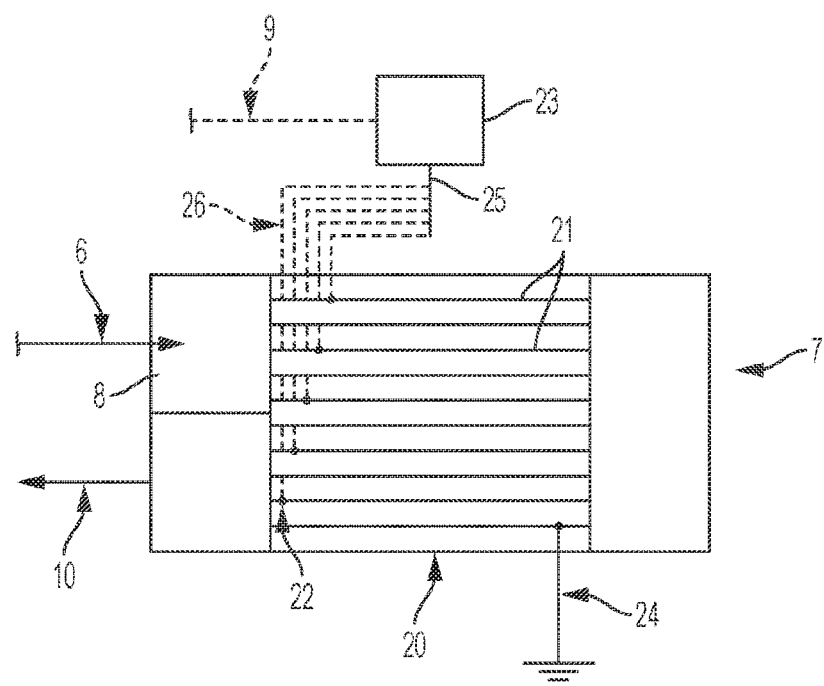
FIG. 2 schematically depicts a reactor of the present invention as useable in the scheme of FIG. 1. The reactor is of a shell and tube configuration where the catalytic surface in contact with the reactants comprises the walls of the tubes. The electrical source includes a transformer to adjust voltage.

FIG. 2 shows a schematic depiction of a shell and tube embodiment of a reactor of the invention. In FIG. 2, reactor 7 comprises shell 20, which can provide containment in the event of a leak, and a series of tubes 21 which are connected to a high voltage source 9 via transformer 23 and busbar 25 to provide a low voltage heater power supply. Electrical leads 26 are connected to the surface of the tubes at connections 22 and provided with ground 24. Watt density is kept to a sufficiently low value, about 30 to about 40 watt/ft, preferably about 35 watt/ft, to provide even heating of the process gas, and to keep tube wall temperature close to the reaction temperature in order to limit coking. To provide even heating, a multiple of tube passes may be employed, each with independently controllable electrically-heated input. Preferably, for alternating current, the electrical heating includes an impedance heating system with the current passing directly through the heater tube wall, utilizing three phase alternating current at low voltage (about 1 to about 90 volts, more preferably about 30 to about 80 volts) and amperage sufficient to achieve the watt density described above. The temperature of the reactor outlet 10 is preferably controlled to about 1° C.

In FIG. 2, vaporized HCFC-244bb feed gas 6 enters at the gas inlet for superheater zone 8 which is also electrically heated. The superheated gas then enters tubes 21. The tubes are constructed of a material, or at least have a surface of such material, which catalyzes the reaction; alternatively or additionally, the tubes may be filled with a packing, such as metal pellets or mesh, which are constructed of a material which catalyzes the reaction. When it is the packing material that catalyzes the reaction, then the packing acts as the catalytic surface that is electrically heated pursuant to the invention.

Figure 4:
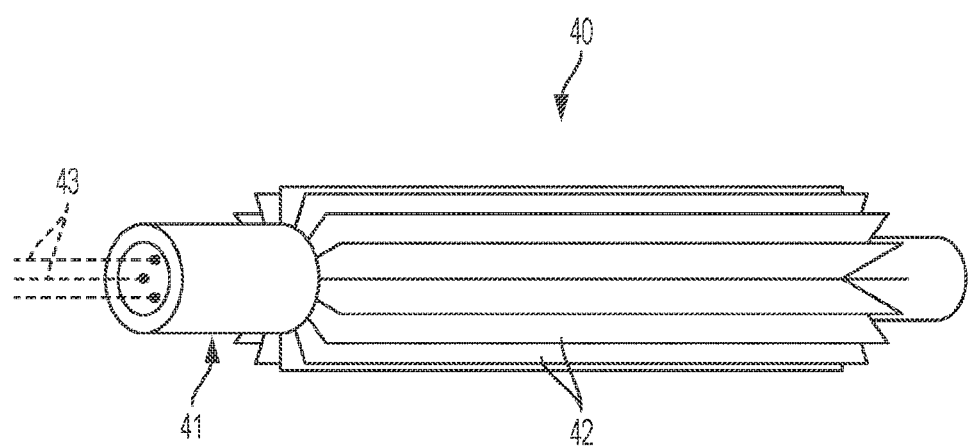
FIG. 4 depicts a finned tube which can be employed as or as part of a reactor in the present invention. The tube sheath and the longitudinal fins comprise the catalytic surface which is heated electrically with the resistance wires shown.

Generally, catalytic materials of construction for the tubes or the packing depend on the reaction contemplated. For example, in the dehydrochlorination of HCFC-244bb to HFO-1234yf, serviceable materials of tube or packing construction include, without limitation, electroless nickel, nickel, stainless steel, Monel® alloys, Inconel® alloys, Incoloy® alloys, Hastelloy® alloys, and combinations thereof. In an embodiment of the present invention, one or more of the tubular elements are finned, such as depicted in FIG. 4, wherein the tubular elements include longitudinal fins 42. However, in other embodiments, none of the tubular elements are finned. Reaction temperatures, that is the temperature to which the electrically heated reactor is operated, also depends on the particular reaction envisioned. For the dehydrochlorination of HCFC-244bb to HFO-1234yf, temperatures can range up to about 700° C., preferably between about 150° and 650° C., with about 400° to about 500° C. more typical, and about 450° to about 480° C. more preferred. Heating can be modulated by adjusting electrical current and/or voltage. Similarly, reactor pressure depends on the reaction; for the conversion of HCFC-244bb to HFO-1234yf, reactor pressure is typically at about 0 psig to about 200 psig, with about 50 to about 100 psig preferred.

In FIG. 1, product comprising HFO-1234yf, HCl, and unreacted HCFC-244bb exits 10 reactor 7 to undergo separation, typically by distillation 11 wherefrom a purified HFO-1234yf product is ultimately collected 12 along, with separated HCl which can be neutralized or recovered 13. A stream of essentially unreacted HCFC-244bb is recycled 5 back to vaporizer 3. In one practice, the separation step consists of two distillation columns in which unreacted HCFC-244bb is separated from the HFO-1234yf product and the HCl in the first column, and the HFO-1234yf product separated from the HCl in a second column. In another practice, the HCl is separated from the HFO-1234yf and recycle HCFC-244bb in the first column, and the HFO-1234yf separated from the recycle HCFC-244bb in the second column.

Figure 3:
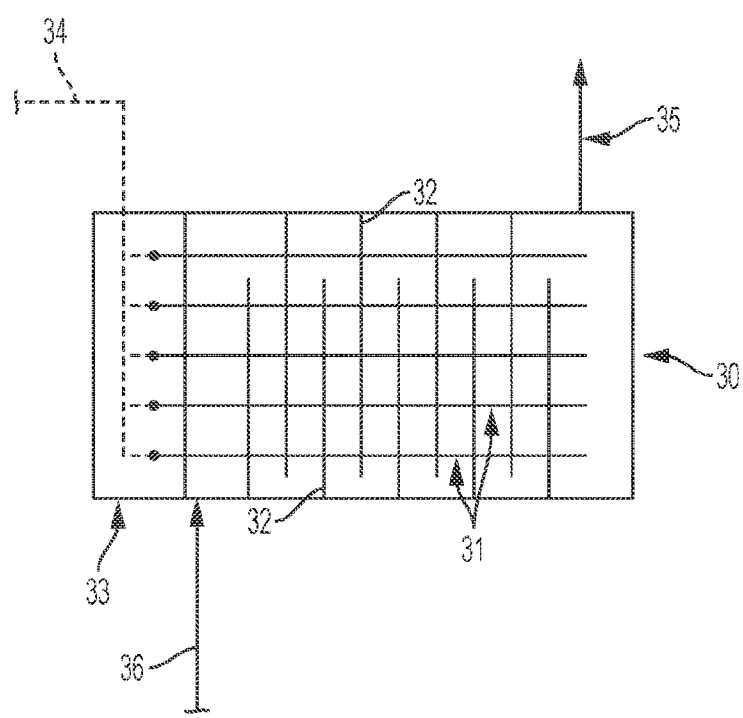
FIG. 3 depicts a schematic embodiment of the present invention where the reactor is a baffled shell and tube configuration.

In another embodiment of the reactor of the invention, FIG. 3, the reactor 30 consists of an apparatus having a reactant gas inlet 36 and product gas outlet 35 and an array of tubular elements 31 heated by electric resistance heating 34 and a terminal heater box 33. The tubular elements are comprised of a material of construction that catalyzes the particular reaction; the process gas passes between these elements within a shell. Reactor 30 has baffles 32 to increase efficiency and to minimize hot spots. The heating elements may optionally utilize the design, shown in FIG. 4, wherein the tubular elements 40 are connected to heating resistance wires 43, and wherein the tubular elements include longitudinal fins 42 (or other shaped protrusions) on the tube sheathing 41 to enhance heat transfer efficiency and also to increase surface area available to catalyze e.g. the dehydrohalogenation reaction.

While the reaction of HCFC-244bb to HFO-1234yf and HCl is the reaction described above, the apparatus described in this invention is not limited to this chemistry and can be used for other endothermic reactions where zero valent metals are used for catalysis or where a catalyst is not required (e.g. pyrolysis). Examples of other such reactions include, without limitation:

$CHX'X''—CY'Y''—CF_3 \rightarrow CH_2=CY—CF_3$ and/or $CHX=CH—CF_3$ where
X and Y=one of H, Cl, F
X' and X''=one or two of H, Cl or F
Y' and Y''=one of H, Cl or F $CH_2=CY—CF_3$ and/or $CHX=CH—CF_3 \rightarrow CH—C—CF_3$ where
X and Y=one of Cl, F Examples of such reactions include:
$CH_2ClCH_2CF_3 \rightarrow CH_2=CH—CF_3+HCl$ (253fb→1243zf+HCl)
$CH_3CHClCF_3 \rightarrow CH_2=CH—CF_3+HCl$ (253db→1243zf+HCl)
$CH_2FCH_2CF_3 \rightarrow CH_2=CH—CF_3+HF$ (254fb→1243zf+HF)
$CH_3CHFCF_3 \rightarrow CH_2=CH—CF_3+HF$ (254eb→1243zf+HF)
$CHCl_2CH_2CF_3 \rightarrow CHCl=CH—CF_3+HCl$ (243fa→1233zd+HCl)
$CH_3CCl_2CF_3 \rightarrow CH_2=CCl—CF_3+HCl$ (243ab→1233xf+HCl)
$CH_2ClCHClCF_3 \rightarrow CH_2=CCl—CF_3/CHCl=CH—CF_3+HCl$ (243db→1233xf/1233zd+HCl)
$CH_2ClCHFCF_3 \rightarrow CH_2=CF—CF_3/CHCl=CH—CF_3+HCl/HF$ (244eb→1234yf/1233zd+HCl/HF)
$CH_2FCHClCF_3 \rightarrow CH_2=CCl—CF_3/CHF=CH—CF_3+HF/HCl$ (244db→1233xf/1234ze+HF/HCl)
$CHFClCH_2CF_3 \rightarrow CHF=CH—CF_3/CHCl=CH—CF3+HCl/HF$ (244fa→1234ze/1233zd+HCl/HF)
$CH_3CF_2CF_3 \rightarrow CH_2=CF—CF_3+HF$ (245cb→1234yf+HF)
$CH_2FCHFCF_3 \rightarrow CH_2=CF—CF_3/CHF=CH—CF_3+HF$ (245eb→1234yf/1234ze+HF)
$CHF_2CH_2CF_3 \rightarrow CHF=CH—CF_3+HF$ (245fa→1234ze+HF)
$CH_2=CCl—CF_3 \rightarrow CH\equiv C—CF_3+HCl$ (1233xf→trifluoropyne+HCl)
$CH_2=CF—CF_3 \rightarrow CH\equiv C—CF_3+HCl$ (1234yf→trifluoropropyne+HF)
$CHCl=CH—CF_3 \rightarrow CH\equiv C—CF_3+HCl$ (1233zd→trifluoropropyne+HCl)
$CHF=CH—CF_3 \rightarrow CH\equiv C—CF_3+HF$ (1234ze→trifluoropropyne+HF)

EXAMPLES

Example 1

In this example, an insulated 1"×0.065" Inconel 625 tube reactor with a 7-point thermocouple of ⅛" OD inserted inside of the tube was used. The distance between two neighboring temperature probe points is 4". The reactor served as the pressure containment vessel, the heating element, and the heat transfer surface. A Flex Kraft Rectifier with maximum output of 5 V and 140 A was used to provide DC (Direct Current) power to the Inconel 625 reactor. Once the hot spot temperature of reactor reached its set point, the flow of 244bb feed was started. During reaction, the reactor effluent was periodically sampled for its compositions.

Table 1 lists its average reactivity under various conditions. An activity higher than that in conventional (externally heated) reactor was observed in this impedance heater reactor. For example, close to 30% 244bb conversion was achieved at temperatures lower than 450° C. In addition, as shown in Table 1, the selectivity to 1234yf was ≥98.5%.

TABLE 1 *

| Period of time, h | Temp. C. | | | | | | | P, psig | 244bb conv., % | Selectivity[#], % | |
|---|---|---|---|---|---|---|---|---|---|---|---|
| | $T_{bottom}$ | $T_1$ | $T_2$ | $T_3$ | $T_4$ | $T_5$ | $T_{top}$ | | | 1234yf | Others |
| 14-34 | 121.0 | 384.7 | 444.0 | 452.9 | 454.1 | 419.5 | 321.5 | 50.0 | 23.3 | 98.8 | 1.2 |
| 36-50 | 115.0 | 383.2 | 441.9 | 448.7 | 440.8 | 395.4 | 299.9 | 70.3 | 25.0 | 98.5 | 1.5 |
| 52-58 | 120.3 | 386.4 | 441.4 | 446.6 | 431.4 | 383.4 | 296.4 | 100.2 | 28.0 | 98.9 | 1.1 |
| 68-88 | 111.9 | 369.4 | 436.2 | 454.7 | 455.8 | 430.5 | 336.0 | 30.2 | 14.8 | 99.4 | 0.6 |
| 91-120 | 105.8 | 368.2 | 433.6 | 450.4 | 444.9 | 405.1 | 308.2 | 49.9 | 14.1 | 99.0 | 1.0 |

TABLE 1 *-continued

| Period of time, h | Temp. C. | | | | | | | P, psig | 244bb conv., % | Selectivity#, % | |
|---|---|---|---|---|---|---|---|---|---|---|---|
| | $T_{bottom}$ | $T_1$ | $T_2$ | $T_3$ | $T_4$ | $T_5$ | $T_{top}$ | | | 1234yf | Others |
| 132-170 | 100.9 | 367.0 | 461.2 | 480.5 | 483.1 | 441.1 | 323.3 | 50.3 | 52.7 | 98.8 | 1.2 |
| 220-241 | 94.2 | 358.6 | 454.2 | 473.8 | 468.3 | 412.8 | 305.1 | 70.2 | 41.8 | 98.7 | 1.3 |

* Other conditions: 45 g/h of average feed rate; organic composition - 94A GC area % 244bb/5.2 GC area % 1233xf/0.5 GC area % 245cb
Calculated assuming no 244bb dehydrofluorination occurred Example 2

The same reactor and set-up as described in Example 1 were used in Example 2. Speed runs were conducted by doubling the feed rate. In one experiment, the feed rate was doubled but the DC input power supply was kept at the same (2.57 V/118.2 A). As shown in Table 2, the doubled feed rate resulted in significant decrease of both hot-spot temperature (from ~468 to ~453° C.) and 244bb conversion (from ~39 to ~11%). Nevertheless, with input power increasing, both hot-spot temperature and 244bb conversion increased. As shown in Table 2, at 2.76 V/126.2 A, the hot-spot temperature and 244bb conversion increased to ~483° C. and ~40%, respectively. In summary, for the doubled feed rate, comparable 244bb conversion was achieved by increasing electrical input power by about 15%.

TABLE 2 *

| Period of time, h | DC power | | Temp. ° C. | | | | | | | P, psig | Flow rate, g/h | 244bb conv., % |
|---|---|---|---|---|---|---|---|---|---|---|---|---|
| | Voltage, V | Current, A | $T_{bottom}$ | $T_1$ | $T_2$ | $T_3$ | $T_4$ | $T_5$ | $T_{top}$ | | | |
| 897-1037 | 7.57 | 118.2 | 85.6 | 356.4 | 447.7 | 467.7 | — | 408.5 | 309.4 | 69.9 | 45.8 | 39.2 |
| 1015-1037 | 2.57 | 118.2 | 47.7 | 259.4 | 397.1 | 453.2 | — | 414.0 | 324.2 | 69.7 | 92.9 | 10.6 |
| 1038-1063 | 2.66 | 122.2 | 43.6 | 282.5 | 419.9 | 470.0 | — | 436.7 | 343.2 | 69.9 | 86.6 | 24.5 |
| 1064-1087 | 2.70 | 124.2 | 43.8 | 289.9 | 430.0 | 477.0 | — | 449.8 | 354.5 | 69.6 | 94.0 | 34.2 |
| 1088-1109 | 2.76 | 126.2 | 42.6 | 298.4 | 438.1 | 483.6 | — | 459.7 | 362.3 | 70.1 | 90.2 | 40.4 |

* Organic composition - 0.8 GC area % 245cb/94.9 GC area % 244bb/4.1 GC area % 1233x Example 3

The same reactor and set-up as described in Example 1 were used in Example 3. The effect of HCl/HF treatments was investigated. The HCl/HF treatments were carried by passing HCl (or HF)/$N_2$ mixed flow through the reactor maintained at high temperatures (see Table 3 for conditions). As shown in Table 3, slightly higher 244bb conversion was observed after HCl/HF treatments while 1234yf selectivity remained almost unchanged. Note that selectivity changeover from 1234yf to 1233xf occurred after similar HF treatment in conventional reactor.

TABLE 3 *

| Period of time, h | Treatment | Temp. ° C. | | | | | | | P, psig | Feed rate, g/h | 244bb conv., % | Selectivity#, % | |
|---|---|---|---|---|---|---|---|---|---|---|---|---|---|
| | | $T_{bottom}$ | $T_1$ | $T_2$ | $T_3$ | $T_4$ | $T_5$ | $T_{top}$ | | | | 1234yf | others |
| 1127-1165 | No | 87.0 | 358.2 | 451.0 | 473.4 | | 403.9 | 306.0 | 68.9 | 45.2 | 28.3 | 99.4 | 0.6 |
| 1169-1189 | In 50% HCl/$N_2$ flow for 16 h at 500° C. | | 356.7 | 450.5 | 472.5 | 459.4 | 404.5 | 312.8 | 69.8 | 44.9 | 30.2 | 99.3 | 0.7 |
| 1193-1363 | In 5% HF/$N_2$ flow for 16 h at 480-490° C. | | 357.2 | 451.1 | 473.4 | 463.6 | 410.2 | 310.7 | 70.0 | 44.0 | 33.9 | 99.4 | 0.6 |

TABLE 3 *-continued

| Period of time, h | Treatment | Temp. °C. | | | | | | | P, psig | Feed rate, g/h | 244bb conv., % | Selectivity#, % | |
|---|---|---|---|---|---|---|---|---|---|---|---|---|---|
| | | $T_{bottom}$ | $T_1$ | $T_2$ | $T_3$ | $T_4$ | $T_5$ | $T_{top}$ | | | | 1234yf | others |
| 1366-1575 | In 5% HF/N$_2$ flow for 25 h at 500-510° C. | 358.3 | 452.2 | 475.0 | 465.0 | 411.8 | 313.9 | | 69.5 | 43.8 | 32.4 | 99.5 | 0.5 |

* Organic composition - 0.8 GC area % 245cb/94.9 GC area % 244bb/4.1 GC area % 1233x
Calculated assuming no 244bb dehydrofluorination occurred Example 4

244bb liquid was vaporized in a steam heated vaporizer at 70 psig pressure and 74° C. It was superheated to 480° C. using an electric superheater, and introduced into the reactor. The reactor consisted of a 2" (51 mm) diameter Alloy 625 tube, directly heated by impedance heating using a 30 volt 3 phase power supply. Watt density was 35 watts/ft$^2$ tube surface area. The reactor was maintained at 480° C. The reactor produced 100 g/hr of HFO-1234yf. The reactor exit gas was cooled and distilled in a two column separation system. The bottom stream from the first column, consisting of unreacted 244bb, was returned to the vaporizer. The overhead stream from the first column passed to the second column, where HCl was withdrawn via the overheads stream, and the HFO-1234yf product withdrawn via the bottoms stream.

The present invention relates to an improved process and reactor design for carrying out reactions necessary to manufacture these compounds, or more particularly a novel heating system for such processes and reactors. The reactor may also be used for other chemical processing that requires heating to high temperatures under carefully controlled conditions. The reactor finds particular use in the manufacture of hydrofluoroolefins (HFOs). The reactor of the invention includes a reactor heated by a specially designed electric heating system.

The foregoing description is by way of example only and is not limiting to the scope of the invention.

What is claimed is:

1. A process for preparing 2,3,3,3-tetrafluoropropene (HFO-1234yf) comprising:
   (a) providing a composition comprising 2-chloro-1,1,1,2-tetrafluorpropane (HCFC-244bb) to a reaction chamber having a catalytic surface in contact with the composition, the reaction chamber being connected to an electrical power source; and
   (b) passing electrical current from the power source through the catalytic surface effective to heat the catalytic surface to a temperature effective to catalytically dehydrochorinate at least a portion of the HCFC-244bb to HFO-1234yf.

2. The process of claim 1 wherein the temperature is about 400° C. to about 500° C.

3. The process of claim 2, wherein the temperature is about 450° C. to about 480° C.

4. The process of claim 1, wherein the reactor pressure is about 0 psig to about 200 psig.

5. The process of claim 1 wherein the catalytic surface in contact with the composition is selected from the group consisting of electroless nickel, nickel, stainless steel, nickel-copper alloy, nickel-chromium alloy, iron-nickel-chromium alloy, nickel-molybdenum alloy, and combinations thereof.

6. The process of claim 1 wherein the reaction chamber is comprised of one or more tubes in a shell and tube configuration, and wherein the catalytic surface in contact with the composition is comprised of an inner wall or an outer wall of said one or more tubes, and the composition comprising HCFC-244bb is superheated to about 400° C. to about 500° C. prior to being provided to the reaction chamber having the catalytic surface.

7. The process of claim 1, wherein the current is alternating current.

8. The process of claim 1, wherein the current is direct current.

9. A process for a dehydrohalogenation reaction comprising
   (a) providing at least one dehydrohalogenation reactant to a reaction chamber, the reaction chamber comprising a surface in contact with said dehydrohalogenation reactant, said surface comprising a material that catalyzes the dehydrohaolgenation reaction; and
   (b) passing electrical current through said surface to heat said surface to a temperature effective to achieve dehydrohalogenation of the dehydrohalogenation reactant.

10. The process of claim 9 wherein the dehydrohalogenation reaction is selected from the group consisting of reactions A, B, C, and combinations thereof:
   A) CHX'X"—CY'Y"—CF$_3$→i) CH$_2$=CY—CF$_3$, or
      ii) CHX=CH—CF$_3$, or
      iii) combinations of i) and ii)
      wherein
      X and Y=one of H, Cl, or F,
      X' and X"=one or two of H, Cl, or F, Y' and Y"=one of H, Cl, or F; or
   B) CH$_2$=CY—CF$_3$→CH≡C—CF$_3$
      wherein X and Y=one of Cl or F; or
   C) CHX=CH—CF$_3$ CH=C—CF$_3$
      wherein X and Y=one of Cl or F.

11. The process of claim 10 wherein the dehydrohalogenation reaction is selected from the group consisting of:
   CH$_2$ClCH$_2$CF$_3$→CH$_2$=CH—CF$_3$+HCl (253fb→1243zf+HCl),
   CH$_3$CHClCF$_3$→CH$_2$=CH—CF$_3$+HCl (253db→1243zf+HCl),
   CH$_2$FCH$_2$CF$_3$→CH$_2$=CH—CF$_3$+HF (254fb→1243zf+HF),
   CH$_3$CHFCF$_3$→CH$_2$=CH—CF$_3$+HF (254eb→1243zf+HF),
   CHCl$_2$CH$_2$CF$_3$→CHCl=CH—CF$_3$+HCl (243fa→1233zd+HCl),
   CH$_3$CCl$_2$CF$_3$→CH$_2$=CCl—CF$_3$+HCl (243ab→1233xf+HCl), $CH_2ClCHClCF_3 \rightarrow CH_2=CCl-CF_3/CHCl=CH-CF_3+HCl$ (243db→1233xf/1233zd+HCl), $CH_2ClCHFCF_3 \rightarrow CH_2=CF-CF_3/CHCl=CH-F_3+HCl/HF$ (244eb→1234yf/1233zd+HCl/HF), $CH_2FCHClCF_3 \rightarrow CH_2=CCl-CF_3/CHF=CH-CF_3+HF/HCl$ (244db→1233xf/1234ze+HF/HCl), $CHFClCH_2CF_3 \rightarrow CHF=CH-CF_3/CHCl=CH-CF3+HCl/HF$ (244fa→1234ze/1233zd+HCl/HF), $CH_3CF_2CF_3 \rightarrow CH_2=CF-CF_3+HF$ (245cb→1234yf+HF), $CH_2FCHFCF_3 \rightarrow CH_2=CF-CF_3/CHF=CH-CF_3+HF$ (245eb→1234yf/1234ze+HF), $CHF_2CH_2CF_3 \rightarrow CHF=CH-CF_3+HF$ (245fa→1234ze+HF), $CH_2=CCl-CF_3 \rightarrow CH\equiv C-CF_3+HCl$ (1233xf→trifluoropyne+HCl), $CH_2=CF-CF_3 \rightarrow CH\equiv C-CF_3+HCl$ (1234yf→trifluoropyne+HF), $CHCl=CH-CF_3 \rightarrow CH\equiv C-CF_3+HCl$ (1233zd→trifluoropropyne+HCl), $CHF=CH-CF_3 \; CH\equiv C-CF_3+HF$ (1234ze trifluoropropyne+HF) and combinations thereof.

12. The process of claim 10, wherein the reactor pressure is about 50 psig to about 100 psig.

13. The process of claim 9 where the temperature is about 400° C. to about 500° C.

14. The process of claim 9 wherein the catalytic surface in contact with the composition is selected from the group consisting of electroless nickel, nickel, stainless steel, nickel-copper alloy, nickel-chromium alloy, iron-nickel-chromium alloy, nickel-molybdenum alloy, and combinations thereof.

15. The process of claim 9 wherein the current is alternating current.

16. The process of claim 9, wherein the current is direct current.

17. The process of claim 9, wherein the reactor pressure is about 0 psig to about 200 psig.

18. The process of claim 10, wherein the reactor pressure is about 50 psig to about 100 psig.

* * * * *